United States Patent [19]

Berg et al.

[11] Patent Number: 4,670,106

[45] Date of Patent: * Jun. 2, 1987

[54] SEPARATION OF N-AMYL ACETATE AND WATER FROM N-AMYL ALCOHOL BY EXTRACTIVE DISTILLATION

[76] Inventors: Lloyd Berg; An-I Yeh, both of 1314 S. Third Ave., Bozeman, Mont. 59715

[*] Notice: The portion of the term of this patent subsequent to Jun. 25, 2002 has been disclaimed.

[21] Appl. No.: 803,332

[22] Filed: Dec. 2, 1985

[51] Int. Cl.$^4$ .................. B01D 3/40; C07C 67/54
[52] U.S. Cl. ......................... 203/51; 203/57; 203/59; 203/60; 203/63; 560/248; 568/913
[58] Field of Search ............... 203/57, 51, 59, 56, 203/60, 63, 14, 18, 19; 560/248, 234; 568/913, 916, 918

[56] References Cited

U.S. PATENT DOCUMENTS

| 1,536,545 | 5/1925 | Willkie | 560/248 |
|---|---|---|---|
| 1,770,414 | 7/1930 | Martin et al. | 560/234 |
| 4,379,028 | 4/1983 | Berg et al. | 203/57 |
| 4,507,176 | 3/1985 | Berg et al. | 203/57 |
| 4,525,245 | 6/1985 | Berg et al. | 203/58 |
| 4,592,805 | 6/1986 | Berg et al. | 203/51 |

FOREIGN PATENT DOCUMENTS

| 1089744 | 9/1960 | Fed. Rep. of Germany | 203/64 |
|---|---|---|---|
| 46701 | 4/1979 | Japan | 560/248 |
| 967471 | 12/1960 | United Kingdom | 203/60 |

*Primary Examiner*—Wilbur Bascomb

[57] ABSTRACT n-Amyl acetate cannot be completely removed from n-amyl acetate - n-amyl alcohol - water mixtures by distillation because of the presence of the minimum ternary azeotrope. n-Amyl acetate can be readily removed from mixtures containing it, n-amyl alcohol and water by using extractive distillation in which the extractive distillation agent is a higher boiling organic compound or a mixture of these. Typical examples of effective agents are dimethylsulfoxide; N,N-dimethylacetamide and dimethylsulfoxide; dimethylformamide, N,N-dimethylacetamide and acetamide.

3 Claims, No Drawings

SEPARATION OF N-AMYL ACETATE AND WATER FROM N-AMYL ALCOHOL BY EXTRACTIVE DISTILLATION

FIELD OF THE INVENTION

This invention relates to a method for separating n-amyl acetate from n-amyl alcohol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture n-amyl acetate is by the catalytic esterification of n-amyl alcohol with acetic acid. n-Amyl acetate (b.p.=148.4° C.), n-amyl alcohol (b.p.=138.1° C.) and water (b.p.=100° C.) form a minimum ternary azeotrope boiling at 94.8° C. and containing 10.5 weight percent n-amyl acetate, 33.3 wt. % n-amyl alcohol and 56.2 wt. % water. n-Amyl acetate forms a binary azeotrope with water boiling at 95.2° C. containing 59 wt. % n-amyl acetate. n-Amyl alcohol also forms a binary minimum azeotrope with water which boils at 95.8° C. and contains 45.6 wt. % n-amyl alcohol. Thus in the esterification of n-amyl alcohol with acetic acid to form n-amyl acetate and water, the rectification of this mixture has two binary and a ternary azeotrope to contend with, and yields the lowest boiling constituent, namely the n-amyl acetate - n-amyl alcohol - water ternary azeotrope. It is therefore impossible to produce n-amyl acetate from n-amyl alcohol and water mixtures by rectification because the lower boiling ternary azeotrope will always come off overhead as the initial product. Any mixture of n-amyl acetate, n-amyl alcohol and water subjected to rectification at one atmosphere pressure will produce an overhead product boiling at 94.8° C. and containing 10.5 wt. % n-amyl acetate, 33.3 wt. % n-amyl alcohol and 56.2 wt. % water. Extractive distillation would be an attractive method of effecting the separation of n-amyl acetate from n-amyl alcohol if agents can be found that (1) will break the n-amyl acetate - n-amyl alcohol - water azeotrope and (2) are easy to recover from the n-amyl alcohol, that is, form no azeotrope with n-amyl alcohol and boil sufficiently above n-amyl alcohol to make the separation by rectification possible with only a few theoretical plates.

Extractive distillation typically requires the addition of an equal amount to twice as much extractive agent as the n-amyl acetate -n-amyl alcohol - water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with n-amyl alcohol otherwise it will form a two-phase azeotrope with the n-amyl alcohol in the recovery column and some other method of separation will have to be employed.

The breaking of this azeotrope by extractive distillation is a new concept. The closest applications of the concept might be the breaking of the methyl acetate - methanol azeotrope described by Berg & Yeh, CHEMICAL ENGINEERING COMMUNICATION, p.3219–3223 and 1984, U.S. Pat. Nos. 4,543,245 and 4,549,938. Berg & Ratanapupech, U.S. Pat. No. 4,379,028 separated ethyl acetate from ethanol. Berg & Yeh, U.S. Pat. Nos. 4,507,176 and 4,525,245 separated n-butyl acetate from n-butanol.

TABLE 1

Extractive Agents Containing Dimethylsulfoxide

| Compounds | Ratios | | Relative Volatilities | |
|---|---|---|---|---|
| Dimethylsulfoxide | 1 | 6/5 | 2.03 | 2.12 |
| Dimethylsulfoxide, Hexamethylene triamine | $(1/2)^2$ | $(3/5)^2$ | 1.13 | 1.78 |
| Dimethylsulfoxide, N,N—Dimethylacetamide | " | " | 2.49 | 2.50 |
| Dimethylsulfoxide, Triethanolamine | " | " | 2.67 | 2.03 |
| Dimethylsulfoxide, Dimethylformamide, Triethanolamine | $(1/3)^3$ | $(2/5)^3$ | 1.90 | 2.12 |
| Dimethylsulfoxide, Dimethylformamide, N,N—Dimethylacetamide | " | " | 2.22 | 2.25 |

TABLE 2

Extractive Agents Containing Amides or Amines

| Compounds | Ratios | | Relative Volatilities | |
|---|---|---|---|---|
| Dimethylformamide | 1 | 6/5 | 1.50 | 1.66 |
| Dimethylformamide, N,N—Dimethylacetamide | (1/2)² | (3/5)² | 1.89 | 2.05 |
| Dimethylformamide, N,N—Dimethylacetamide, Acetamide | (1/3)³ | (2/5)³ | 2.07 | 2.10 |
| Dimethylformamide, Triethanolamine, Acetamide | " | " | 1.52 | 1.93 |
| N,N—Dimethylacetamide | 1 | 6/5 | 1.88 | 1.85 |
| Triethanolamine | " | " | 2.55 | 1.72 |
| Acetamide, N,N—Dimethylacetamide | (1/2)² | (3/5)² | 1.71 | 2.03 |

OBJECTIVE OF THE INVENTION

The object of this invention is to provide a process or method of extractive distillation that will enhance the relative volatility of n-amyl acetate from n-amyl alcohol in their separation in a rectification column. It is a further object of this invention to identify suitable extractive distillation agents which will eliminate the n-amyl acetate-n-amyl alcohol - water ternary azeotrope and make possible the production of pure n-amyl acetate and n-amyl alcohol by rectification. It is a further object of this invention to identify organic compounds which in addition to the above constraints, are stable, can be separated from n-amyl alcohol by rectification with relatively few theoretical plates and can be recycled to the extractive distillation column and reused with little decomposition.

SUMMARY OF THE INVENTION

The objects of the invention are provided by a process for separating n-amyl acetate from n-amyl alcohol which entails the use of certain oxygenated, nitrogenous and/or sulfur containing organic compounds in extractive distillation.

DETAILED DESCRIPTION OF THE INVENTION

We have discovered that dimethylsulfoxide (DMSO), dimethylformamide (DMFA), N,N-dimethylacetamide and triethanolamine, both individually and as mixtures, will effectively negate the n-amyl acetate - n-amyl alcohol - water ternary azeotrope and permit the separation of pure n-amyl acetate from n-amyl alcohol by rectification when employed as the agent in extractive distillation. Tables 1 and 2 list the compounds, mixtures and approximate proportions that we have found to be effective. The data in Tables 1 and 2 were obtained in a vapor-liquid equilibrium still. In each case, the starting material was the n-amyl acetate - n-amyl alcohol - water azeotrope. The ratios are the parts by weight of extractive agent used per part of n-amyl acetate -n-amyl alcohol - water azeotrope. The relative volatilities are listed for each of the two ratios employed. The compounds that are effective when used alone are DMSO, DMFA, N,N-dimethylacetamide and triethanolamine. The compounds which are effective when used in mixtures of two or more are acetamide and hexamethylene diamine. The two relative volatilities shown in Tables 1 and 2 correspond to the two different ratios investigated. For example, in Table 1, one part of DMSO with one part of the n-amyl acetate - n-amyl - water azeotrope gives a relative volatility of 2.03, 6/5 parts of DMSO give 2.12. One half part of DMSO mixed with one half part of N,N-dimethylacetamide with one part of the n-amyl acetate - n-amyl alcohol - water azeotrope gives a relative volatility of 2.49, 3/5 parts of DMSO plus 3/5 parts of N,N-dimethylacetamide gives 2.50. One third part of DMFA plus ⅓ part of N,N-dimethylacetamide plus ⅓ part of acetamide with one part of the n-amyl acetate - n-amyl alcohol - water azeotrope gives a relative volatility of 2.07, with 3/5 parts, these three give a relative volatility of 2.10. In every example in Tables 1 and 2, the starting material is the n-amyl acetate - n-amyl alcohol - water azeotrope which possesses a relative volatility of 1.00.

TABLE 2

Data From Run Made In Rectification Column

| Agent | Wt. % n-Amyl Overhead | Acetate Bottoms | Relative Volatility |
|---|---|---|---|
| Dimethylsulfoxide | 95.15 | 19.15 | 2.67 |

Notes:
Ternary mixture comprised 22 wt. % n-amyl acetate, 71 wt. % n-amyl alcohol, 7 wt. % water.
Agent added at 20 ml/min.
Reflux Rate was 10–16ml/min.

Dimethylsulfoxide (DMSO), one of the compounds listed in Table 1 whose relative volatility had been determined in the vapor-liquid equilibrium still, was then evaluated in a glass perforated plate rectification column possessing 4.5 theoretical plates. The n-amyl acetate - n-amyl alcohol - water mixture charged to the stillpot was 22 wt. % n-amyl acetate, 71 wt. % n-amyl alcohol and 7 wt. % water. The ratio of n-amyl acetate to n-amyl alcohol in the overhead is greater than 2.4 and the results are tabulated in Table 2. Without the extractive agent, the overhead would be the azeotrope whose ratio of n-amyl acetate to n-amyl alcohol is 2.4. This proves that the extractive agent is negating the azeotrope and makes the rectification proceed as if the azeotrope no longer existed and brings the more volatile components, n-amyl acetate and water, out as overhead products. It is our belief that this is the first time that this has been accomplished for this azeotrope.

The data in Table 2 was obtained in the following manner. The charge was 22 wt. % n-amyl acetate, 71 wt. % n-amyl alcohol and 7 wt. % water and after a half hour of operation in the 4.5 theoretical plate column to establish equilibrium, dimethylsulfoxide at 95° C. and 10–16ml/min. was pumped in. The rectification was continued for about two hours with sampling of the overhead and bottoms after one hour, 1.5 hours and two hours. The average of the three analyses is shown in Table 2 and was 95.15% n-amyl acetate in the overhead and 19.15% n-amyl acetate in the bottoms, both on a water-free basis which gives a relative volatility of 2.67 of n-amyl acetate to n-amyl alcohol. This indicates that the ternary azeotrope has been negated and the separation accomplished. The n-amyl acetate comes off in the form of its binary azeotrope with water which on condensation, immediately forms two layers. The solubility of n-amyl acetate in liquid water is only 0.1%.

THE USEFULNESS OF THE INVENTION

The usefulness or utility of this invention can be demonstrated by referring to the data presented in Tables 1 and 2. All of the successful extractive distillation agents show that n-amyl acetate, n-amyl alcohol and water can be separated from their ternary azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity n-amyl acetate from any mixture of these three including the ternary azeotrope. The stability of the compounds used and the boiling point difference is such that complete recovery and recycle is obtainable by a simple distillation and the amount required for make-up is small.

WORKING EXAMPLES

Example 1

The n-amyl acetate - n-amyl alcohol - water azeotrope is 10.5-wt. % n-amyl acetate, 33.3 wt. % n-amyl alcohol and 56.2 wt. % water. Fifty grams of the n-amyl acetate - n-amyl alcohol - water azeotrope and fifty grams of dimethylsulfoxide (DMSO) were charged to an Othmer type vapor-liquid equilibrium still and refluxed for 15 hours. Analysis of the vapor and liquid by gas chromatography gave a vapor composition of 28.1% n-amyl acetate, 62.5% n-amyl alcohol; a liquid composition of 16.7% n-amyl acetate, 75% n-amyl alcohol. This indicates a relative volatility of 2.03. Ten grams of DMSO were added and refluxing continued for another 12 hours. Analysis indicated a vapor composition of 27.4% n-amyl acetate, 64.4% n-amyl alcohol; a liquid composition of 15.6% n-amyl acetate, 77.9% n-amyl alcohol which is a relative volatility of 2.12.

Example 2

Fifty grams of the n-amyl acetate - n-amyl alcohol - water azeotrope, 25 grams of DMSO and 25 grams of N,N-dimethylacetamide were charged to the vapor-liquid equilibrium still and refluxed for eleven hours. Analysis indicated a vapor composition of 17.1% n-amyl acetate, 66.7% n-amyl alcohol; a liquid composition of 8.2% n-amyl acetate, 80% n-amyl alcohol which is a relative volatility of 2.49. Five grams of DMSO and five grams of N,N-dimethylacetamide were added and refluxing continued for another 12 hours. Analysis indicated a vapor composition of 14.8% n-amyl acetate, 70.4% n-amyl alcohol; a liquid composition of 7.1% n-amyl acetate, 83.7% n-amyl alcohol which is a relative volatility of 2.50.

Example 3

Fifty grams of the n-amyl acetate - n-amyl alcohol - water azeotrope, 17 grams of dimethylformamide (DMFA), 17 grams of N,N-dimethylacetamide and 17 grams of acetamide were charged to the vapor-liquid equilibrium still and refluxed for 16 hours. Analysis indicated a vapor composition of 16.8% n-amyl acetate, 69.1% n-amyl alcohol; a liquid composition of 9.4% n-amyl acetate, 80% n-amyl alcohol which is a relative volatility of 2.07. Three grams each of DMFA, N,N-di methylacetamide and acetamide were added and refluxing continued for another five hours. Analysis indicated a vapor composition of 17.4% n-amyl acetate, 68.7% n-amyl alcohol; a liquid composition of 9.3% n-amyl acetate, 80.8% n-amyl alcohol which is a relative volatility of 2.10.

Example 4

A glass perforated plate rectification column was calibrated with ethylbenzene and p-xylene which possesses a relative volatility of 1.06 and found to have 4.5 theoretical plates. A solution comprising 88 grams of n-amyl acetate, 285 grams of n-amyl alcohol and 28 grams of water was placed in the stillpot and heated. When refluxing began, an extractive agent consisting of pure DMSO was pumped into the column at a rate of 20 ml/min. The temperature of the extractive agent as it entered the column was 95° C. After establishing the feed rate of the extractive agent, the heat input to the n-amyl acetate - n-amyl alcohol - water in the stillpot was adjusted to give a total reflux rate of 10–16 ml/min. After 75 minutes of steady operation, the overhead and bottoms samples of approximately two ml. were collected and analysed using gas chromatography. The overhead analysis was 94.29% n-amyl acetate, 5.71% n-amyl alcohol. The bottoms analysis was 19.48% n-amyl acetate, 80.52% n-amyl alcohol. Using these compositions in the Fenske equation, with the number of theoretical plates being 4.5, gave an average relative volatility of 2.56 for each theoretical plate. After 105 minutes of steady operation, overhead and bottoms samples were again taken and analysed. The overhead composition was 96.01% n-amyl acetate, 3.99% n-amyl alcohol; the bottoms composition was 18.82% n-amyl acetate, 81.18% n-amyl alcohol which is a relative volatility of 2.81 for each theoretical plate.

The nature of the present invention having been described, what we wish to claim as new and useful and secure by Letters Patent is:

1. A method for recovering n-amyl acetate and water from a mixture of n-amyl acetate, n-amyl alcohol and water which comprises distilling a mixture of n-amyl acetate, n-amyl alcohol and water in a rectification column in the presence of about one part of extractive agent per part of n-amyl acetate - n-amyl alcohol - water mixture, recovering n-amyl acetate and water as overhead product, obtaining the n-amyl alcohol and the extractive agent from the stillpot and separating the n-amyl alcohol from the extractive agent in another rectification column, the extractive agent comprises dimethylsulfoxide.

2. The method of claim 1 in which the extractive agent comprises a mixture of dimethylsulfoxide and at least one material from the group consisting of dimethylformamide, triethanolamine, N,N-dimethylacetamide and hexamethylene triamine.

3. A method for recovering n-amyl acetate and water from a mixture of n-amyl acetate, n-amyl alcohol and water which comprises distilling a mixture of n-amyl acetate, n-amyl alcohol and water in a rectification column in the presence of about one part of extractive agent per part of n-amyl acetate -n-amyl alcohol - water mixture, recovering n-amyl acetate and water as overhead product, obtaining the n-amyl alcohol and the extractive agent from the stillpot and separating the n-amyl alcohol from the extractive agent in another rectification column, the extractive agent comprises triethanolamine.

* * * * *